(12) United States Patent
Mohan et al.

(10) Patent No.: US 10,542,977 B2
(45) Date of Patent: *Jan. 28, 2020

(54) SURGICAL LOADING UNITS AND MOUNTING MEMBERS THEREOF

(71) Applicant: Covidien LP, Mansfield, MA (US)

(72) Inventors: Venkata Ramana Mohan, Hyderabad (IN); Rajasekhar Nukala, Secunderabad (IN)

(73) Assignee: COVIDIEN LP, Mansfield, MA (US)

( * ) Notice: Subject to any disclaimer, the term of this patent is extended or adjusted under 35 U.S.C. 154(b) by 290 days.

This patent is subject to a terminal disclaimer.

(21) Appl. No.: 15/646,530

(22) Filed: Jul. 11, 2017

(65) Prior Publication Data

US 2017/0303919 A1 Oct. 26, 2017

Related U.S. Application Data

(63) Continuation of application No. 14/503,458, filed on Oct. 1, 2014, now Pat. No. 9,700,316.

(51) Int. Cl.
*A61B 17/072* (2006.01)
*A61B 17/00* (2006.01)
*A61B 90/00* (2016.01)

(52) U.S. Cl.
CPC ...... *A61B 17/072* (2013.01); *A61B 17/07207* (2013.01); *A61B 2017/00477* (2013.01); *A61B 2017/00526* (2013.01); *A61B 2017/07214* (2013.01); *A61B 2017/07221* (2013.01); *A61B 2017/07264* (2013.01); *A61B 2017/07271* (2013.01); *A61B 2090/036* (2016.02)

(58) Field of Classification Search
CPC ... A61B 17/072; A61B 17/3209; A61B 17/00; A61B 90/00

USPC ... 227/176.1, 175.1, 19, 180.1, 179.1, 178.1
See application file for complete search history.

(56) References Cited

U.S. PATENT DOCUMENTS

| | | |
|---|---|---|
| 1,295,769 A | 2/1919 | Kux |
| 2,560,786 A | 7/1951 | Wright et al. |
| 4,215,194 A | 7/1980 | Shepherd |

(Continued)

FOREIGN PATENT DOCUMENTS

| | | |
|---|---|---|
| EP | 2617369 A1 | 7/2013 |
| EP | 2772211 A2 | 9/2014 |
| EP | 2777532 A2 | 9/2014 |

OTHER PUBLICATIONS

"Steel Rule Dies", Machinery's Handbook, 26th Ed. Oberg, et al., 2000; pp. 1315-1317.

(Continued)

*Primary Examiner* — Nathaniel C Chukwurah
(74) *Attorney, Agent, or Firm* — Carter, DeLuca & Farrell, LLP

(57) ABSTRACT

A mounting member for a surgical stapler is fabricated from a plastic. The mounting member has a proximal end portion and a distal end portion. The proximal end portion has a pair of vertical projections configured to be coupled to a proximal body portion of a loading unit of a surgical stapler. The distal end portion includes a pair of walls extending distally from the proximal end portion. Each wall has a boss and a strut. The boss defines a transverse bore therethrough configured to be rotatably coupled to a cartridge assembly of the loading unit. The strut extends from the proximal end portion to the boss.

16 Claims, 5 Drawing Sheets

(56) References Cited

U.S. PATENT DOCUMENTS

| | | | |
|---|---|---|---|
| 5,083,449 | A | 1/1992 | Kobayashi et al. |
| 5,100,042 | A | 3/1992 | Gravener et al. |
| 5,797,539 | A | 8/1998 | Wilde et al. |
| 6,412,325 | B1 | 7/2002 | Croswell |
| 6,640,605 | B2 | 11/2003 | Gitlin et al. |
| 7,328,829 | B2 | 2/2008 | Arad et al. |
| 8,215,532 | B2 | 7/2012 | Marczyk |
| 8,360,298 | B2 | 1/2013 | Farascioni et al. |
| 8,459,521 | B2 | 6/2013 | Zemlok et al. |
| 9,700,316 | B2 * | 7/2017 | Mohan ................. A61B 17/072 |
| 2004/0092373 | A1 | 5/2004 | Petersen |
| 2005/0113821 | A1 | 5/2005 | Pendekanti et al. |
| 2008/0041916 | A1 | 2/2008 | Milliman et al. |
| 2008/0105730 | A1 | 5/2008 | Racenet et al. |
| 2008/0110960 | A1 | 5/2008 | Jankowski |
| 2008/0142565 | A1 | 6/2008 | Ehrenfels et al. |
| 2009/0050671 | A1 | 2/2009 | Racenet et al. |
| 2009/0272785 | A1 | 11/2009 | Sonnenschein et al. |
| 2010/0193566 | A1 | 8/2010 | Scheib et al. |
| 2010/0213238 | A1 * | 8/2010 | Farascioni ....... A61B 17/07207 227/176.1 |
| 2013/0098969 | A1 | 4/2013 | Scirica et al. |
| 2013/0206816 | A1 | 8/2013 | Penna |

OTHER PUBLICATIONS

European Search Report, dated Feb. 3, 2016, corresponding to European Application No. 151875261.7; 7 pages.

\* cited by examiner

SURGICAL LOADING UNITS AND MOUNTING MEMBERS THEREOF

CROSS-REFERENCE TO RELATED APPLICATIONS

The present application is a Continuation Application which claims that benefit of and priority to U.S. patent application Ser. No. 14/503,458, filed on Oct. 1, 2014, now U.S. Pat. 9,700,316, the entire content of which is incorporated herein by reference.

BACKGROUND

Technical Field

The present disclosure relates generally to instruments for surgically joining and cutting tissue and, more specifically, to surgical instruments having curved or straight jaw members and loading units for use therewith.

Background of Related Art

Various types of surgical instruments used to surgically join tissue are known in the art, and are commonly used, for example, for closure of tissue or organs in transection, resection, anastomoses, for occlusion of organs in thoracic and abdominal procedures, and for mechanically sealing tissue.

One example of such a surgical instrument is a surgical stapling instrument, which may include an anvil assembly, a cartridge assembly for supporting an array of surgical staples, an approximation mechanism for approximating the cartridge and anvil assemblies, and a firing mechanism for ejecting the surgical staples from the cartridge assembly.

When using a surgical stapling instrument, it is common for a surgeon to approximate the anvil and cartridge assemblies. Next, the surgeon can fire the surgical stapling instrument to emplace staples in tissue. Additionally, the surgeon may use the same instrument or a separate instrument to cut the tissue adjacent or between the row(s) of staples.

Presently, a component or components used to rotatably couple the cartridge and/or anvil assembly to a body of the surgical stapling instrument is constructed from stainless steel using a complex manufacturing process.

SUMMARY

In one embodiment of the present disclosure, a mounting member for a surgical stapler is provided. The mounting member includes a body fabricated from a plastic and defines a longitudinal axis. The body includes a proximal end portion and a distal end portion. The proximal end portion has a pair of vertical projections configured to be coupled to a proximal body portion of a loading unit of a surgical stapler. The distal end portion includes a pair of walls, a boss, and a strut. The walls extend distally from the proximal end portion. The boss is coupled to one wall of the pair of walls and defines a bore therethrough configured to be rotatably coupled to a cartridge assembly of a loading unit. The strut extends from the proximal end portion to the boss.

In embodiments, the plastic may be polyetheretherketone. The polyetheretherketone may be carbon filled or glass filled.

In embodiments, the boss may be cylindrical and extend perpendicularly from the wall of the pair of walls.

In embodiments, the body may be monolithically formed.

In embodiments, the proximal end portion of the body may further include a convex outer surface and a raised section centrally disposed on the convex outer surface.

In embodiments, the pair of vertical projections, the pair of walls, and the strut may have a uniform thickness equal to one other.

In embodiments, the cartridge assembly may be curved.

In another aspect of the present disclosure, a loading unit is provided. The loading unit includes a proximal body portion defining a longitudinal axis, a tool assembly, and a mounting member. The tool assembly extends distally from the proximal body portion and includes a cartridge assembly and an anvil assembly fixed to a distal end of the proximal body portion. The mounting member is fabricated from a plastic and includes a body and a fastener. The body includes a proximal end portion a distal end portion. The proximal end portion has a pair of vertical projections coupled to the distal end of the proximal body portion. The distal end portion includes a pair of walls, a boss, and a strut. The walls extend distally from the proximal end portion. The boss is coupled to a wall of the pair of walls and defines a bore therethrough. The strut extends from the proximal end portion to the boss. The fastener of the mounting member extends through the cartridge assembly and the bore of the boss to rotatably couple the cartridge assembly to the mounting member.

In embodiments, the cartridge assembly and the anvil assembly may have a curved configuration.

BRIEF DESCRIPTION OF FIGURES

Various embodiments of the presently disclosed surgical instrument are disclosed herein with reference to the drawings, wherein.

DETAILED DESCRIPTION

Figure 1A:
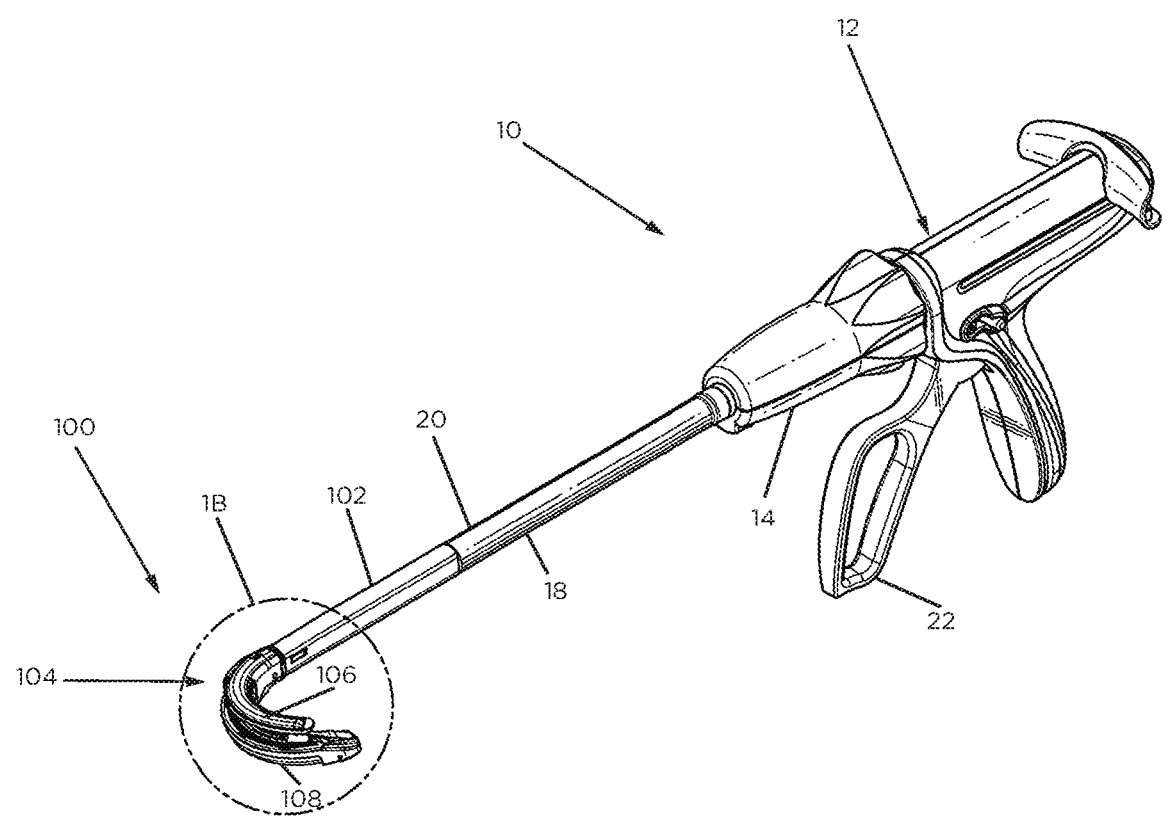
FIG. 1A is a perspective view of a surgical stapler including a loading unit in accordance with the present disclosure.

Embodiments of the presently disclosed surgical stapler including a loading unit having a proximal body portion, a tool assembly, and a mounting member for rotatably coupling component(s) of the tool assembly to the proximal body portion are described in detail with reference to the drawings, wherein like reference numerals designate corresponding elements in each of the several views. As is common in the art, the term 'proximal" refers to that part or component closer to the user or operator, e.g., surgeon or physician, while the term "distal" refers to that part or component farther away from the user.

With reference to FIG. 1A, a surgical stapler of the present disclosure is indicated as reference numeral 10 having a curved tool assembly 104 disposed at a distal end thereof. While not explicitly shown, the present application may also relate to surgical stapling instruments having parallel jaw members and to electrosurgical instruments used to join tissue. Surgical stapler 10 includes a handle assembly 12 having a movable trigger 22, a rotating mechanism 14, an elongated or endoscopic portion 18, and a disposable loading unit (or "DLU") 100. Endoscopic portion 18 extends distally from rotating mechanism 14. Loading unit 100 is attachable to a distal end of endoscopic portion 18 of surgical stapler 10, e.g., to allow surgical stapler 10 to have greater versatility. Loading unit 100 may be configured for a single use and/or may be configured to be used more than once. Examples of loading units for use with a surgical stapling instrument are disclosed in commonly-owned U.S. Pat. No. 8,360,298 to Farascioni et al., the entire contents of which are incorporated by reference herein.

With reference to FIGS. 1B-5, loading unit 100 includes a proximal body portion 102, a mounting member 200 (FIGS. 2-5), and a tool assembly 104. Proximal body portion 102 defines a longitudinal axis "X1," and is releasably attachable to a distal end 20 of endoscopic portion 18 (FIG. 1A) of surgical stapler 10. Tool assembly 104 includes a pair of jaw members, such as, for example, an anvil assembly 106 and a cartridge assembly 108, as described in greater detail below. Mounting member 200 couples proximal body portion 102 of loading unit 100 to cartridge assembly 108 of tool assembly 104 such that cartridge assembly 108 is pivotable relative to anvil assembly 106.

Figure 3:
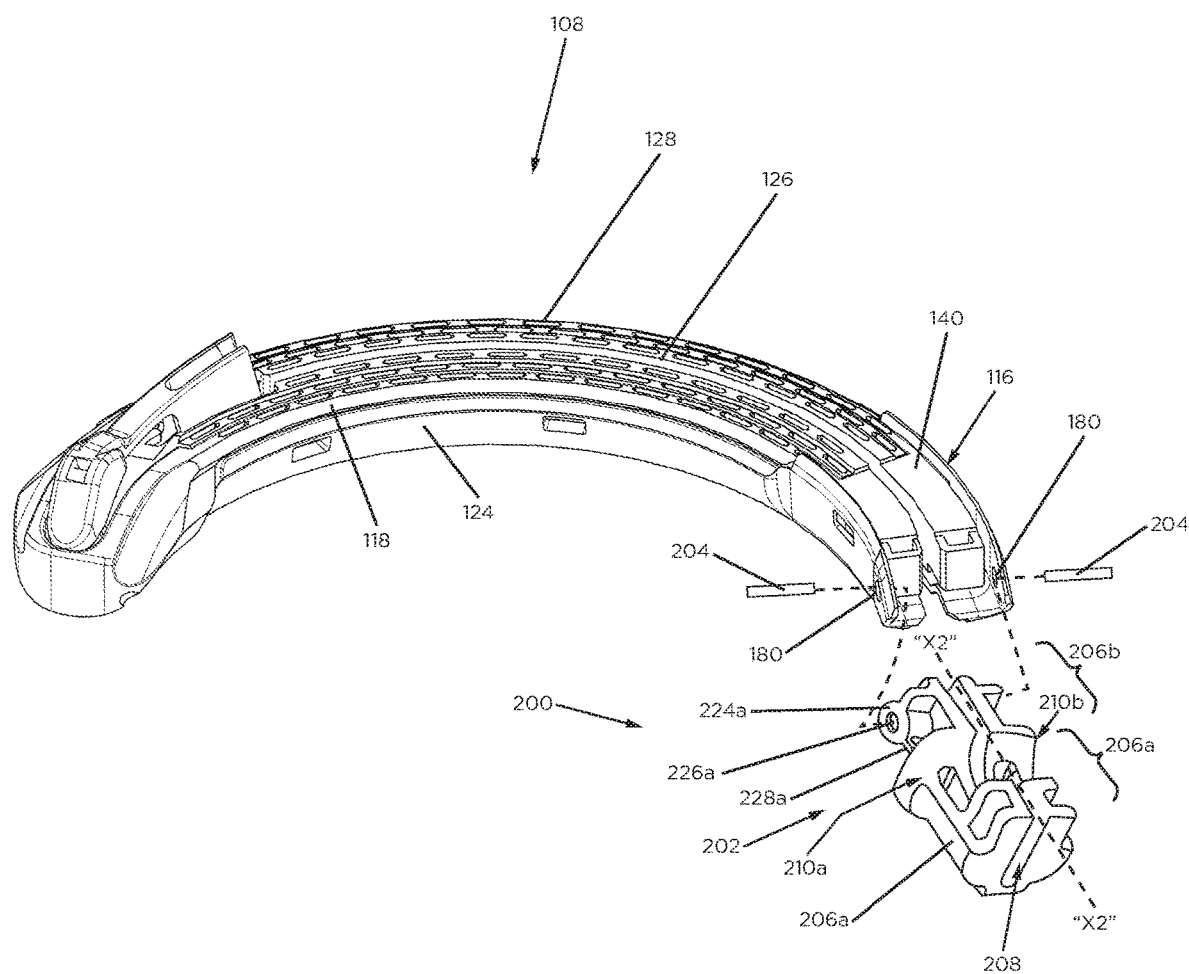
FIG. 3 is a perspective view, with parts separated, of a cartridge assembly and a mounting member of the tool assembly of FIG. 1B.
Figure 4:
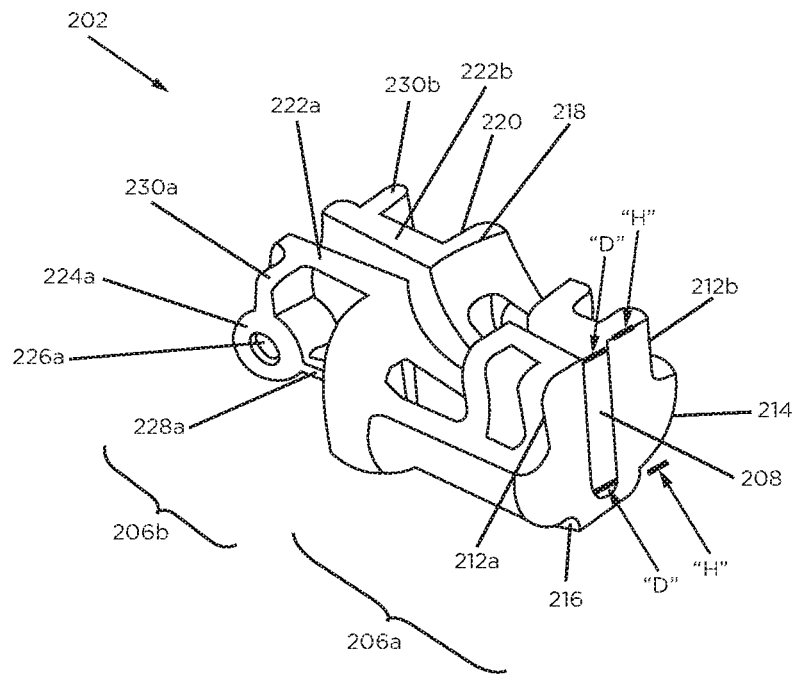
FIG. 4 is a top, perspective view of the mounting member of FIG. 3.
Figure 5:
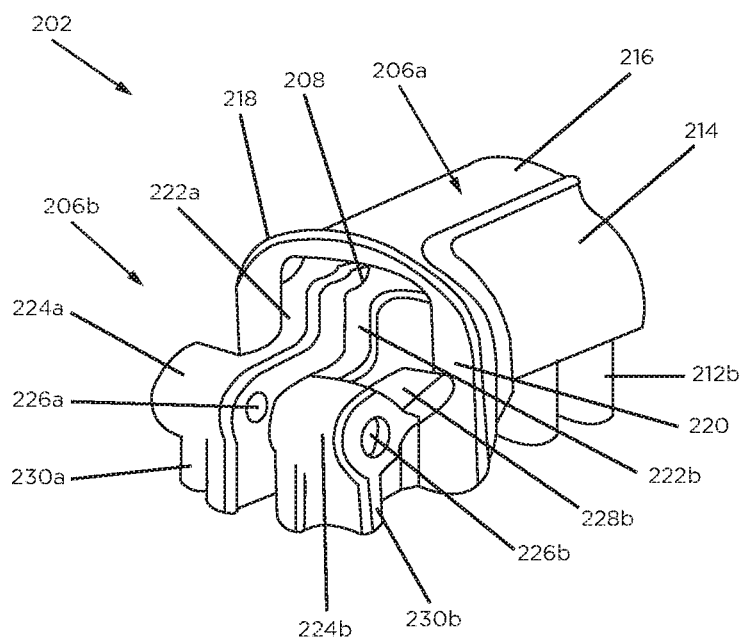
FIG. 5 is a bottom, perspective view of the mounting member of FIG. 3.

With reference to FIGS. 3-5, mounting member 200 includes a body 202, fabricated from a plastic material, and a pair of fasteners 204 used to pivotably interconnect mounting member 200 with cartridge assembly 108 of tool assembly 104. Body 202 may be formed via plastic injection molding using various plastics, such as, for example, thermoplastics such as carbon filled or glass filled polyetheretherketone (PEEK), including polyaryletherketone (PAEK), polyetherketoneketone (PEKK) and polyetherketone (PEK).

Body 202 may be fabricated from material composites, including the above materials, to achieve various desired characteristics such as strength, rigidity, elasticity, compliance, and durability. Body 202 may also be fabricated from a heterogeneous material such as a combination of two or more of the above-described materials. Body 202 may be monolithically formed, integrally connected, or include fastening elements and/or instruments. The advantages of fabricating body 202 from one or more of the materials described above, for example, PEEK, are, for example, a reduction in the number of complex machining operations of body 202, increased strength and stiffness with superior wear and chemical resistant properties, and lower manufacturing cost.

With continued reference to FIGS. 3-5, body 202 of mounting member 200 has a proximal end portion 206a and a distal end portion 206b defining a longitudinal axis "X2" therebetween, which is coaxial with longitudinal axis "X1" of proximal body portion 102 of loading unit 100 upon coupling mounting member 200 with proximal body portion 102. Body 202 has a generally elongated configuration. In embodiments, body 202 may be variously configured, such as, for example, rectangular, oblong, uniform, non-uniform, tapered, and/or polygonal. Body 202 has a channel 208 extending along longitudinal axis "X2" from a proximal-most end of proximal end portion 206a to a distal-most end of distal end portion 206b splitting body 202 into two, symmetrical half-sections 210a, 210b. Channel 208 has a depth "D" less than a height "H" of body 202 (FIG. 4); however, it is contemplated that depth "D" of channel 208 and height "H" of body 202 are approximately equal. Channel 208 is configured for slidable receipt of a drive assembly 360, as described in greater detail below.

Proximal end portion 206a of mounting member 200 has a pair of vertical projections 212a, 212b extending upwardly from body 202. Each of vertical projections 212a, 212b has a rectangular configuration and a U-shaped transverse cross section. Vertical projections 212a, 212b are configured to be coupled to proximal body portion 102 (FIG. 2) of loading unit 100 by frictionally fitting into corresponding recesses (not shown) in a half-section 103a of proximal body portion 102. In some embodiments, vertical projections 212a, 212b may be secured to half-section 103a of proximal body portion 102 via various fastening engagements, such as, for example, adhesives, snap-fit engagement, and/or fasteners.

Proximal end portion 206a of mounting member 200 further includes a convex outer surface 214 and a raised section 216 centrally disposed on convex outer surface 214. Raised section 216 strengthens proximal end portion 206a, adds rigidity, and reduces deformation under loads to maintain its original configuration. Channel 208 extends through body 202 to convex outer surface 214, terminating adjacent raised section 216. Proximal end portion 206a has a planar portion 218 in perpendicular relation to convex outer surface 216. Planar portion 218 has a planar face 220 oriented in a distal direction.

Distal end portion 206b of mounting member 200 extends distally from planar face 220 of proximal end portion 206a. Distal end portion 206b includes a pair of walls 222a, 222b in parallel relation to one another and spaced from one another by a width of channel 208. Each wall 222a, 222b has a stepped configuration. Distal end portion 206b includes a pair of bosses 224a, 224b supported on a respective wall 222a, 222b. Bosses 224a, 224b extend perpendicularly from a respective wall 222a, 222b, outwardly from one another and away from channel 208.

As illustrated in FIG. 3, bosses 224a, 224b are configured to be positioned into a proximal end of a carrier 116 of cartridge assembly 108 that receives and supports a longitudinally curved cartridge 118 of cartridge assembly 108. Each boss 224a, 224b defines a bore 226a, 226b therethrough extending perpendicular to longitudinal axis "X2" of body 202 of mounting member 200. When mounting member 200 is disposed in the proximal end of carrier 116 of cartridge assembly 108, each bore 226a, 226b is aligned with a hole 180 formed in the carrier 116 of cartridge assembly 108 such that mounting member 200 is pivotally secured to carrier 116 by fastener 204 of mounting member 200. In this way, cartridge assembly 108 is pivotably coupled to proximal end portion 102 of loading unit 100 via mounting member 200. In embodiments, fastener 204 may be variously configured, such, as, for example, a self-tapping screw or a pivot pin. In embodiments, one fastener 204 is used to extend through both bosses 224a, 224b.

Distal end portion 206b of body 202 of mounting member 200 includes a first pair of struts 228a, 228b. Each of the first pair of struts 228a, 228b extends from planar surface 220 of proximal end portion 206a to a proximally-facing side of a respective boss 224a, 224b to resist flexion of walls 222a, 222b relative to planar surface 220. Each wall 222a, 222b includes a second pair of struts 230a, 230b extending from an upwardly facing side of a respective boss 224a, 224b. Struts 230a, 230b resist flexion of bosses 224a, 224b relative to walls 222a, 222b and maintains channel 208 open for drive member 360 to freely translate proximally and distally and minimize binding.

As shown in FIG. 4, each component of body 202, for example, vertical projections 212a, 212b, walls 222a, 222b, bosses 224a, 224b, and struts 228a, 228b, 230a, 230b, is constructed from one, continuous, monolithically formed wall having a uniform thickness throughout provided during manufacturing of body 202 of mounting member 200. As such, one piece of plastic may be used to manufacture body 202 and the number of steps required to manufacture body 202 is reduced.

Figure 1B:
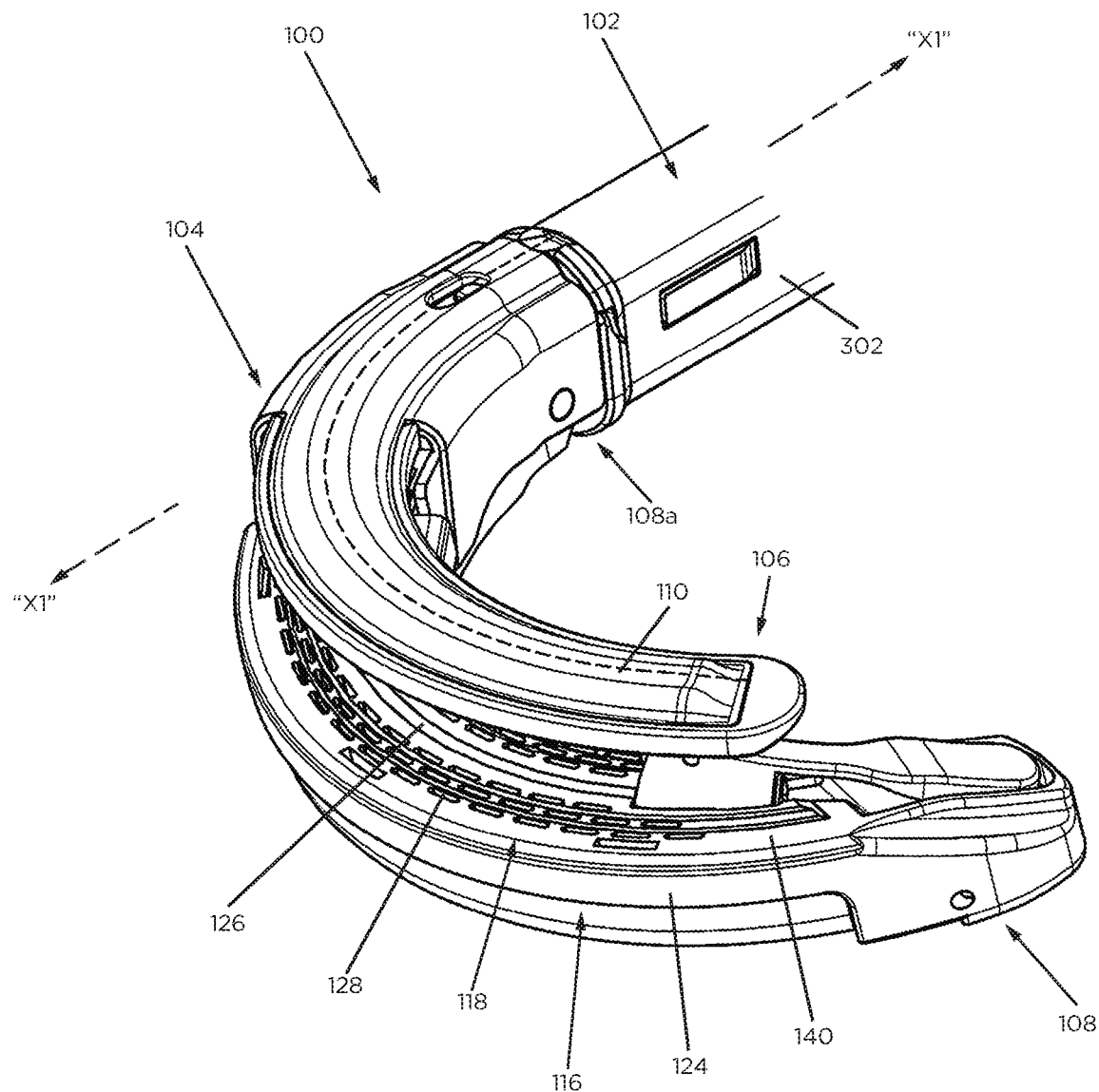
FIG. 1B is an enlarged view of the area of detail of FIG. 1A illustrating the loading unit including a tool assembly and a proximal body portion.
Figure 2:
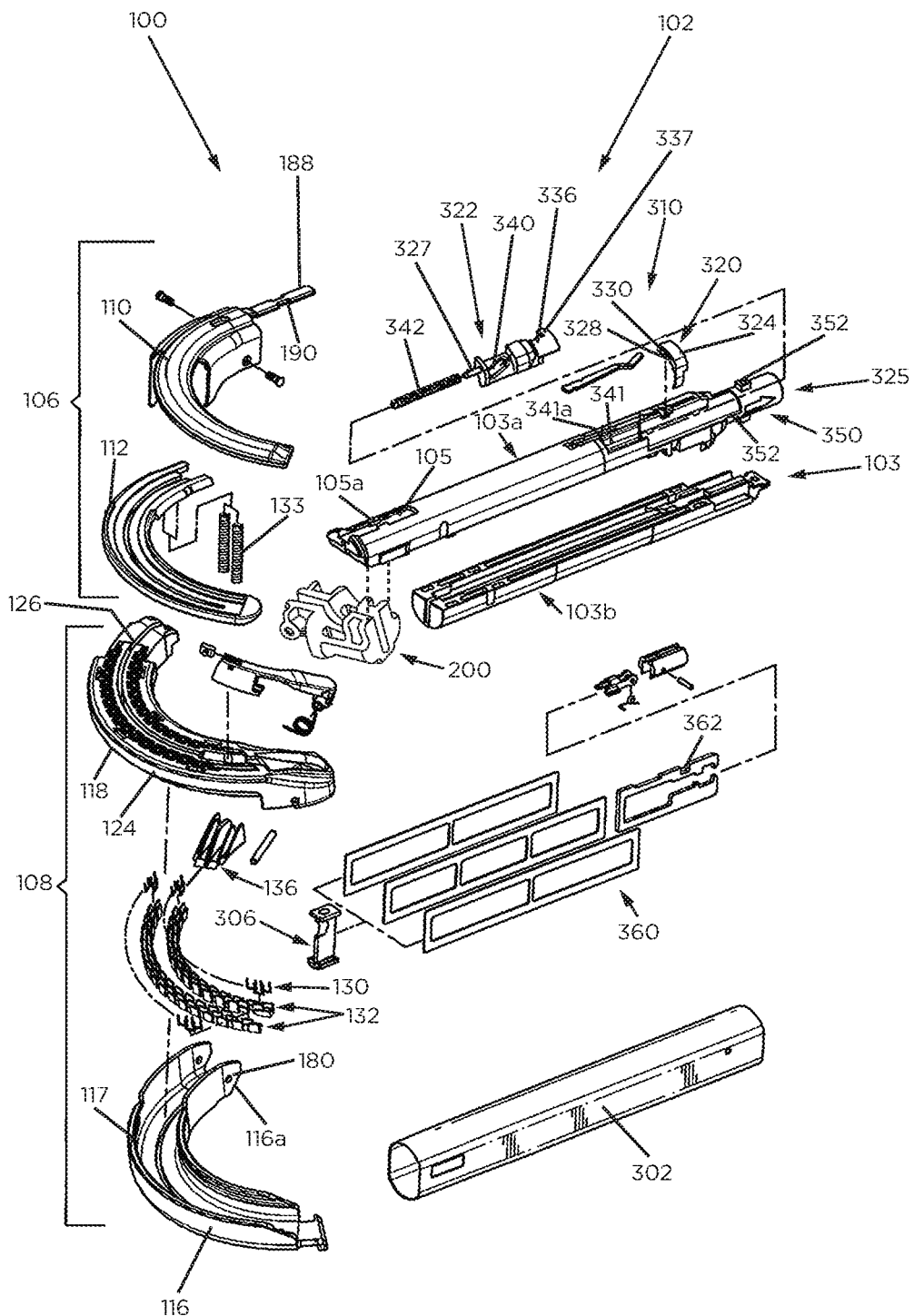
FIG. 2 is an exploded view of the loading unit of FIG. 1A

With reference to FIGS. 1B, 2, and 3, each of anvil assembly 106 and cartridge assembly 108 is longitudinally curved. That is, anvil assembly 106 and cartridge assembly 108 are curved with respect to the longitudinal axis "X1" defined by proximal body portion 102. As used herein with respect to curved parts of the surgical stapler 10 of the present disclosure, the term "distal," which typically refers to that part or component of the instrument that is farther away from the user, refers to the portion of the curved part that is farthest along an axis that follows the curve of the curved part. That is, while an intermediate portion of a curved part may be farther from the user during use, the portion of the curved part that is farthest along its axis is considered "distal."

In disclosed embodiments, the radius of curvature of both anvil assembly 106 and cartridge assembly 108 is between about 1.00 inches and about 2.00 inches, and in particular, may be approximately 1.40 inches. The curved jaw members, as compared to straight jaw members, may help facilitate access to lower pelvis regions, e.g., during lower anterior resection ("LAR"). Additionally, the inclusion of curved jaw members may allow increased visualization to a surgical site and may also allow more room for a surgeon to manipulate target tissue or the jaw members themselves with his or her hand.

One jaw member is pivotal in relation to the other. In the illustrated embodiments, cartridge assembly 108 is pivotal in relation to anvil assembly 106 and is movable between an open or unclamped position and a closed or approximated position via mounting member 200, as described above. Cartridge assembly 108 is urged in the open position via a biasing member, e.g., a pair of compression springs 133 (FIG. 2) disposed between an anvil cover 110 of anvil assembly 106 and cartridge 118 of cartridge assembly 108 (FIG. 2).

With reference to FIG. 2, anvil assembly 106 includes longitudinally curved anvil cover 110 and a longitudinally curved anvil plate 112, which includes a plurality of staple forming depressions (not shown). In embodiments, the radius of curvature of both anvil cover 110 and anvil plate 112 is between about 1.00 inches and about 2.00 inches, and in particular, may be approximately 1.40 inches. Anvil plate 112 is secured to an underside of anvil cover 110 to define a channel (not shown) between plate 112 and cover 110. When tool assembly 104 is in the approximated position, the staple forming depressions (not shown) are positioned in juxtaposed alignment with cartridge assembly 108.

With continued reference to FIGS. 1B, 2, and 3, cartridge assembly 108 includes a longitudinally curved channel or carrier 116 which receives and supports longitudinally curved cartridge 118. Cartridge 118 can be attached to carrier 116 by adhesives, a snap-fit connection, or other connection. In embodiments, the radius of curvature of both carrier 116 and cartridge 118 is between about 1.00 inches and about 2.00 inches, and in particular, may be approximately 1.40 inches. Cartridge 118 includes a pair of support struts 124 which rest on sidewalls 117 of carrier 116 to stabilize cartridge 118 on carrier 116. Support struts 124 also set the height or location of cartridge 118 with respect to anvil plate 112. An external surface of carrier 116 includes an angled cam surface 116a.

Cartridge 118 defines a plurality of laterally spaced staple retention slots 128, which are configured as holes in a tissue contacting surface 140 of cartridge 118. Each slot 128 is configured to receive a staple 130 therein. Cartridge 118 also defines a plurality of cam wedge slots (not shown), which accommodate staple pushers 132 and which are open on the bottom (i.e., away from tissue contacting surface 140) to allow a longitudinally curved actuation sled 136 to pass therethrough.

With reference to FIG. 2, staple cartridge 118 includes a central longitudinally curved slot 126, and three longitudinally curved rows of staple retention slots 128 positioned on each side of curved longitudinal slot 126. In embodiments, the radius of curvature of both slot 126 and pusher 132 is between about 1.00 inches and about 2.00 inches, and in particular, may be approximately 1.40 inches. More specifically, actuation sled 136 passes through the cam wedge slots (not shown) defined in cartridge 118 and forces staple pushers 132 towards respective staples 130. Staples 130 are then forced out of their respective staple retention slots 128.

With continued reference to FIG. 2, proximal body portion 102 of loading unit 100 includes an inner body 103 formed from molded half-sections 103a and 103b, an outer body 302, a drive assembly 360, and a drive locking assembly 310. Inner body 103 is coupled to cartridge assembly 108 by mounting member 200, as described above. Inner body 103 is coupled to anvil assembly 106, as described below. The illustrated embodiment of anvil cover 110 includes a proximally extending finger 188 having a pair of cutouts 190 formed therein. Cutouts 190 are positioned on each lateral side of finger 188 to help secure anvil cover 110 to half-section 103a. More particularly, half-section 103a includes a channel 105 therein, and channel 105 includes a pair of protrusions 105a. Finger 188 of anvil cover 110 mechanically engages channel 105 of half-section 103a, such that cutouts 190 are aligned with protrusions 105a. Outer body 302 of proximal body portion 102 covers finger 188 and channel 105. The configuration of finger 188 and channel 105 facilitates a secure connection between anvil cover 110 and half-section 103a. Moreover, this connection results in a non-movable (e.g., non-pivotable) engagement of anvil assembly 106 with proximal body portion 102.

Loading unit 100 includes a locking mechanism 310 including a locking member 320 and a locking member actuator 322. Locking member 320 is rotatably supported within a longitudinal or transverse slot 325 formed in a proximal portion of upper housing half 103a of inner body 103 of loading unit 100. Locking member 320 is movable from a first position, in which locking member 320 maintains drive assembly 360 in a prefired position, to a second position, in which drive assembly 360 is free to move axially.

Locking member 320 includes a semi-cylindrical body 324 which is slidably positioned within transverse slot 325 formed in upper housing half 103a of body portion 103. Cylindrical body 324 includes a radially inwardly extending cam member 328 and a radially inwardly extending finger 330. Finger 330 is dimensioned to be received within a notch 362 formed in drive assembly 360. Engagement of finger 330 in notch 362 of drive assembly 360 prevents drive assembly 360 from moving linearly within proximal body portion 103 to prevent actuation of loading unit 100 prior to attachment of loading unit 100 to endoscopic portion 18 of surgical stapler 10.

Locking member actuator 322 is slidably positioned within axial slot 325 formed in upper housing half section 103a of body portion 103 of loading unit 100. Actuator 322 includes a proximal abutment member 336, a distal spring guide 327, and a central cam slot 340. An axial slot 341 in the housing half section 103a intersects transverse slot 325 such that cam member 328 of locking member 320 is slidably positioned within cam slot 340 of locking member actuator 322. A biasing member or spring 342 is positioned about spring guide 327 between a distal surface of actuator 322 and a wall 341a defining the distal end of axial slot 341. Spring 342 urges actuator 322 to a first position within axial slot 341. In the first position, abutment member 336 is positioned on an insertion tip 350 of proximal body portion 102 and cam slot 340 is positioned to locate cam member 328 such that finger 330 of lock member 320 is positioned within notch 362 of drive assembly 360.

Prior to attachment of loading unit 100 onto endoscopic portion 18 of surgical stapler 10, spring 342 urges actuator 322 to the first position to maintain lock member 320 in its first position as discussed above. When insertion tip 350 of loading unit 100 is linearly inserted into the open end of endoscopic portion 18 (FIG. 2) of surgical stapler 10, nubs 352 of insertion tip 350 move linearly through slots (not shown) formed in the open end of endoscopic portion 18. As nubs 352 pass through the slots, the proximal end of abutment member 336, which is angularly offset from nubs 352, abuts a wall of endoscopic portion 18 defining the slots for receiving nubs 352 of proximal body portion 103 of loading unit 300. As loading unit 100 is moved farther into endoscopic portion 18, locking member actuator 322 is moved from its first position to its second position. As actuator 322 is moved to its second position, lock member 320 is cammed from its first position engaged with notch 362 of drive assembly 360 to its second position to move finger 330 from notch 362. Locking mechanism 310 including locking member 320 and locking member actuator 322 prevents advancement of drive assembly 360 of loading unit 100 prior to loading of loading unit 100 onto endoscopic portion 18.

Locking member actuator 322 includes an articulation lock portion 337 disposed thereon. In particular, articulation lock portion 337 extends in an approximate right angle from abutment member 336. Articulation lock portion 337 is configured to physically prevent the longitudinal translation of an articulation member (not shown) of handle assembly 12 (FIG. 1A) of surgical stapler 10. That is, even when loading unit 100 is engaged with endoscopic portion 18, articulation lock portion 337 of loading unit 100 prevents the articulation member from entering loading unit 100.

During operation of stapler 10, actuation of its movable handle 22 through successive strokes causes distal advancement of its drive bar (not shown), such that the drive bar pushes drive assembly 360 through cartridge 118. (Further details of how actuation of movable handle 22 causes distal advancement of the drive bar is explained in U.S. Pat. No. 6,953,139 to Milliman et al., the entire contents of which is incorporated by reference herein.) The movement of drive assembly 360 moves longitudinally curved actuation sled 136 through cartridge 118. As sled 136 moves through cartridge 118, actuation sled 136 sequentially engages pushers 132 to move pushers 132 vertically within staple retention slots 128 and eject staples 130 into the staple forming depressions (not shown) of anvil plate 112. Subsequent to the ejection of staples 130 from retention slots 128 (and into tissue), a dynamic clamping member or knife 306 severs the stapled tissue as knife 306 travels through curved slot 126 of cartridge 118.

The present disclosure also relates methods of using the described surgical stapler 10 to perform a lower anterior resection. Such a method includes providing surgical stapler 10, positioning jaw members adjacent tissue, approximating one jaw member (e.g., cartridge assembly 108) with respect to the other jaw member (e.g., anvil assembly 106), advancing drive assembly 360 such that knife 306 and at least a portion of drive assembly 360 move along a curvilinear path to cause staples 130 to be ejected into tissue and to cut tissue . In certain embodiments, the jaw members are approximated, and the interior of the intestinal tissue is then washed out or otherwise cleansed. The tissue is then cut and stapled. In this way, the interior intestinal tissue is cleansed up to the location of the jaw members.

While the above description contains many specifics, these specifics should not be construed as limitations on the scope of the present disclosure, but merely as illustrations of various embodiments thereof. Therefore, the above description should not be construed as limiting, but merely as exemplifications of various embodiments. Those skilled in the art will envision other modifications within the scope and spirit of the claims appended hereto.

The invention claimed is:

1. A surgical stapling device, comprising:
   a pair of surgical stapling jaws, one of the jaws being a cartridge assembly having a staple driving assembly, the pair of jaws being longitudinally curved;
   a mounting member having a body fabricated from a plastic and defining a longitudinal axis, the body including:
      a proximal end portion having a pair of vertical projections configured to be coupled to a proximal body portion of the surgical stapling jaws;
      a distal end portion including a pair of walls and a boss coupled to one wall of the pair of walls and defining a bore therethrough configured to be rotatably coupled to the cartridge assembly; and
      a strut extending from the proximal end portion to the boss.

2. The surgical stapling device according to claim 1, wherein the plastic is polyetheretherketone.

3. The surgical stapling device according to claim 2, wherein the polyetheretherketone is at least one of carbon filled or glass filled.

4. The surgical stapling device according to claim 1, wherein the boss is cylindrical and extends perpendicularly from the one wall of the pair of walls.

5. The surgical stapling device according to claim 1, wherein the body is monolithically formed.

6. The surgical stapling device according to claim 1, wherein the proximal end portion of the body further includes:
   a convex outer surface; and
   a raised section centrally disposed on the convex outer surface.

7. The surgical stapling device according to claim 1, wherein the pair of vertical projections, the pair of walls, and the strut have a uniform thickness equal to one other.

8. A surgical stapling device, comprising:
   a pair of surgical stapling jaws, one of the jaws being a cartridge assembly having a staple driving assembly, the pair of jaws being longitudinally curved; and a mounting member having a body fabricated from polyetheretherketone and defining a longitudinal axis, the body including:
- a proximal end portion having a pair of vertical projections configured to be coupled to a proximal body portion of the surgical stapling jaws; and
- a distal end portion including a pair of walls and a boss coupled to one wall of the pair of walls and defining a bore therethrough configured to be rotatably coupled to the cartridge assembly.

9. The surgical stapling device according to claim 8, wherein the polyetheretherketone is at least one of carbon filled or glass filled.

10. The surgical stapling device according to claim 8, wherein the boss is cylindrical and extends perpendicularly from the one wall of the pair of walls.

11. The surgical stapling device according to claim 8, wherein the body is monolithically formed.

12. A surgical stapling device, comprising:
- a pair of surgical stapling jaws, one of the jaws being a cartridge assembly having a staple driving assembly, the pair of jaws being longitudinally curved; and
- a mounting member having a body fabricated from a plastic and defining a longitudinal axis, the body including:
  - a proximal end portion having:
    - a pair of vertical projections configured to be coupled to a proximal body portion of the surgical stapling jaws;
    - a convex outer surface; and
    - a raised section centrally disposed on the convex outer surface; and
  - a distal end portion including a pair of walls and a boss coupled to one wall of the pair of walls and defining a bore therethrough configured to be rotatably coupled to the cartridge assembly.

13. The surgical stapling device according to claim 12, wherein the plastic is polyetheretherketone.

14. The surgical stapling device according to claim 13, wherein the polyetheretherketone is at least one of carbon filled or glass filled.

15. The surgical stapling device according to claim 12, wherein the boss is cylindrical and extends perpendicularly from the one wall of the pair of walls.

16. The surgical stapling device according to claim 12, wherein the body is monolithically formed.

* * * * *